United States Patent [19]

Love

[11] 4,008,602
[45] Feb. 22, 1977

[54] ULTRASONIC TESTING OF MULTILAYER CERAMIC CAPACITORS

[75] Inventor: Gordon R. Love, Greenville, S.C.

[73] Assignee: Union Carbide Corporation, New York, N.Y.

[22] Filed: Oct. 23, 1973

[21] Appl. No.: 408,420

[52] U.S. Cl. .............................. 73/67.8 R
[51] Int. Cl.² ........................... G01N 29/04
[58] Field of Search .......... 73/67.8 R, 67.8 S, 67.9, 73/67.5 R, 67.6, 71.5 US; 29/593, 25.42, 59.3; 317/242, 261

[56] References Cited

UNITED STATES PATENTS

| | | | |
|---|---|---|---|
| 2,903,886 | 9/1959 | Renaut | 73/67.8 R X |
| 3,011,339 | 12/1961 | Furon | 73/67.9 |
| 3,036,151 | 5/1962 | Mitchell | 73/67.8 S |
| 3,223,905 | 12/1965 | Fabricius | 317/261 |
| 3,423,991 | 1/1969 | Collins | 73/67.5 R |
| 3,509,752 | 5/1970 | Moore | 73/67.9 |
| 3,534,590 | 10/1970 | Kent et al. | 73/67.8 R X |
| 3,548,641 | 12/1970 | Mitchell | 73/67.9 |
| 3,553,805 | 1/1971 | Didinger | 29/593 X |
| 3,575,043 | 4/1971 | Allen et al. | 73/67.8 S |

Primary Examiner—Herbert Goldstein
Assistant Examiner—Stephen A. Kreitman
Attorney, Agent, or Firm—Fredrick J. McCarthy, Jr.

[57] ABSTRACT

Ultrasonic testing method for detecting detrimental internal voids in ceramic capacitors.

6 Claims, 9 Drawing Figures

ULTRASONIC TESTING OF MULTILAYER CERAMIC CAPACITORS

The present invention is directed to the testing of multilayer ceramic capacitors for detrimental internal voids such as, fracture fissures and delamination defects, e.g., undesired separation of electrode and/or dielectric materials in ceramic capacitors. More particularly, the present invention is directed to a method employing ultrasonic energy in the detection of detrimental internal voids in ceramic capacitors.

Multilayer monolithic ceramic capacitor chips applied either directly in hybrid circuits or with leads and encapsulation on printed circuit boards are widely used in electronic applications such as computers, communications systems and medical electronics. These capacitors, as is known in the art, comprise a plurality of very thin planar metal electrodes arranged in a stack separated by and embedded in a ceramic dielectric most commonly consisting essentially of barium titanate.

By way of general description, the manufacture of ceramic capacitors involves the preparation of a "green" sheet of ceramic powder, typically 15 to 100 microns thick, containing a small amount of organic binder. Electrodes are printed from precious metal particle inks, e.g., submicron alloy particles of gold - 25% palladium alloy in an organic vehicle on the ceramic sheet from which they are stacked, laminated under pressure and subsequently fired. In the course of firing, organic binder materials are removed. The dielectric is sintered into a single dense ceramic body and the electrode metal particles are sintered to provide a coherent metal layer, e.g., 0.1 to 0.5 mils thick. The long term reliability of ceramic capacitors is very important in view of the applications involved, and it has been found as a result of extensive testing and examination that the delayed failure of the multilayer ceramic capacitor can be related to the occurrence of internal voids in manufactured capacitors. Such detrimental internal voids involve the physical separation of adjacent electrode and dielectric material, and fracture fissures in the capacitor body.

It is known that capacitor bodies containing such defects are three or more times more likely to fail under given test or service conditions than identical parts which contain no such defects Gordon Love - Nondestructive Testing of Monolithic Ceramic Capacitors -ISHM 1973, International Microelectronics Symposium - Oct. 22, 1973.

Previous attempts to improve the reliability of populations of ceramic capacitors which may contain internal defects have consisted of either (a) destructive testing of a sample from the population, e.g., by metallographic cross sectioning to determine the presence of voids in the sample, or, (b) "burning-in" the capacitors, usually under high voltage and temperature stresses to induce a failure in capacitors with defects. Each of these methods has severe limitations which are overcome by the method of the present invention. The destructive tests only provide information about the presence of defects in the parts which are destroyed. One might assume that the remainder of the population from which the sample is taken will have a similar characteristic, but the technique does not permit nondestructive sorting of the defect-containing capacitors from defect-free capacitors. Furthermore, it is time consuming and costly because capacitors are destroyed. The method of "burning-in" capacitors has been applied with good success to other types of capacitors, e.g., U.S. Pat. No. 3,553,805. Its application to multilayer ceramic capacitors is severely limited, however, because very long times are required to achieve significant improvements in reliability by inducing the poorest capacitors to fail. In other words, it is more difficult to accelerate the mode of failure which the capacitor would exhibit during use life without causing undesired side effects such as new failure modes in a multilayer ceramic capacitor than in a solid tantalum or organic film capacitor. Previous attempts at detection of such delaminations, during or after manufacture, without destruction of the capacitor, has involved complicated X-ray and liquid crystal techniques of uncertain large scale reliability.

It is therefore an object of the present invention to provide a non-destructive, relatively simple and highly reliable method for detecting detrimental internal voids in multilayer ceramic capacitors.

Other objects will be apparent from the following description and claims taken in conjunction with the drawing in which FIG. 1 shows schematically a ceramic capacitor body having a representative internal void in the form of a delamination defect.

The present invention involves the utilization of ultrasonic energy transmission through a non-homogeneous path in a multilayer ceramic capacitor to detect the presence of detrimental internal voids in such capacitors.

Figure 1:
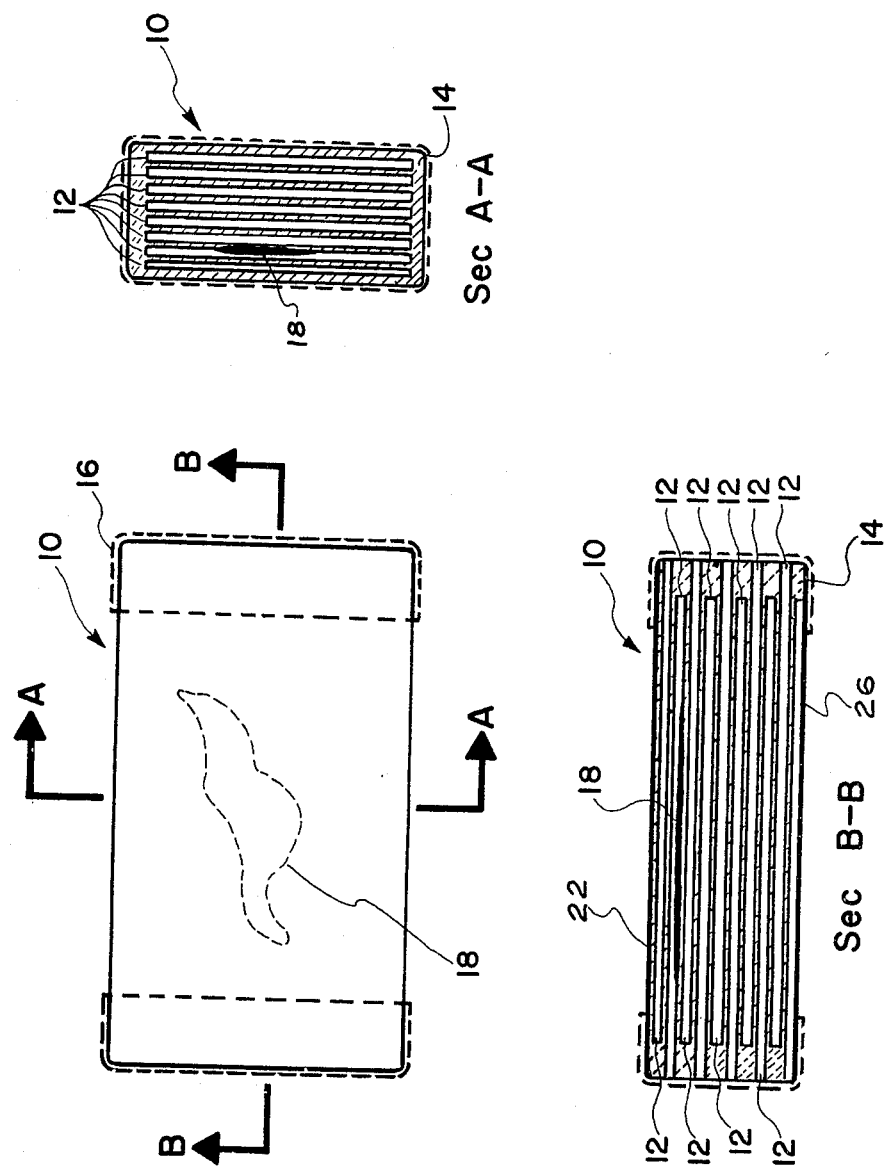

With reference to the drawing, FIG. 1 indicates at 10 an orthogonally shaped ceramic capacitor body manufactured in the conventional manner previously described having parallel metal electrodes 12 which are parallel to the opposed surfaces 22 and 26 and are separated by and enclosed within ceramic dielectric 14. Adjacent electrodes are ultimately provided with separate electrical connectors, usually by the known technique of metallization, as indicated at 16. The number of electrodes is commonly about 5 to 100 each having a thickness of about 2.0 to 10.0 microns with the thickness of the separating dielectric layer being about 15 to 100 microns depending on design considerations. In the practice of the present invention, it is not necessary for the capacitor to have the specific orthogonal shape indicated in FIG. 1, provided that the capacitor has two opposed parallel faces parallel with the electrodes of the capacitor.

An internal void in the form of a lamination defect is indicated at 18 and is representative of the type of defect to be detected by the method of the present invention, i.e., separation voids. Such voids can extend substantially the full length or width of the capacitor body or can be as small as 1 mm and less, e.g., than 100 microns, in length or width and can have a thickness of 5 microns or more.

Figure 2:
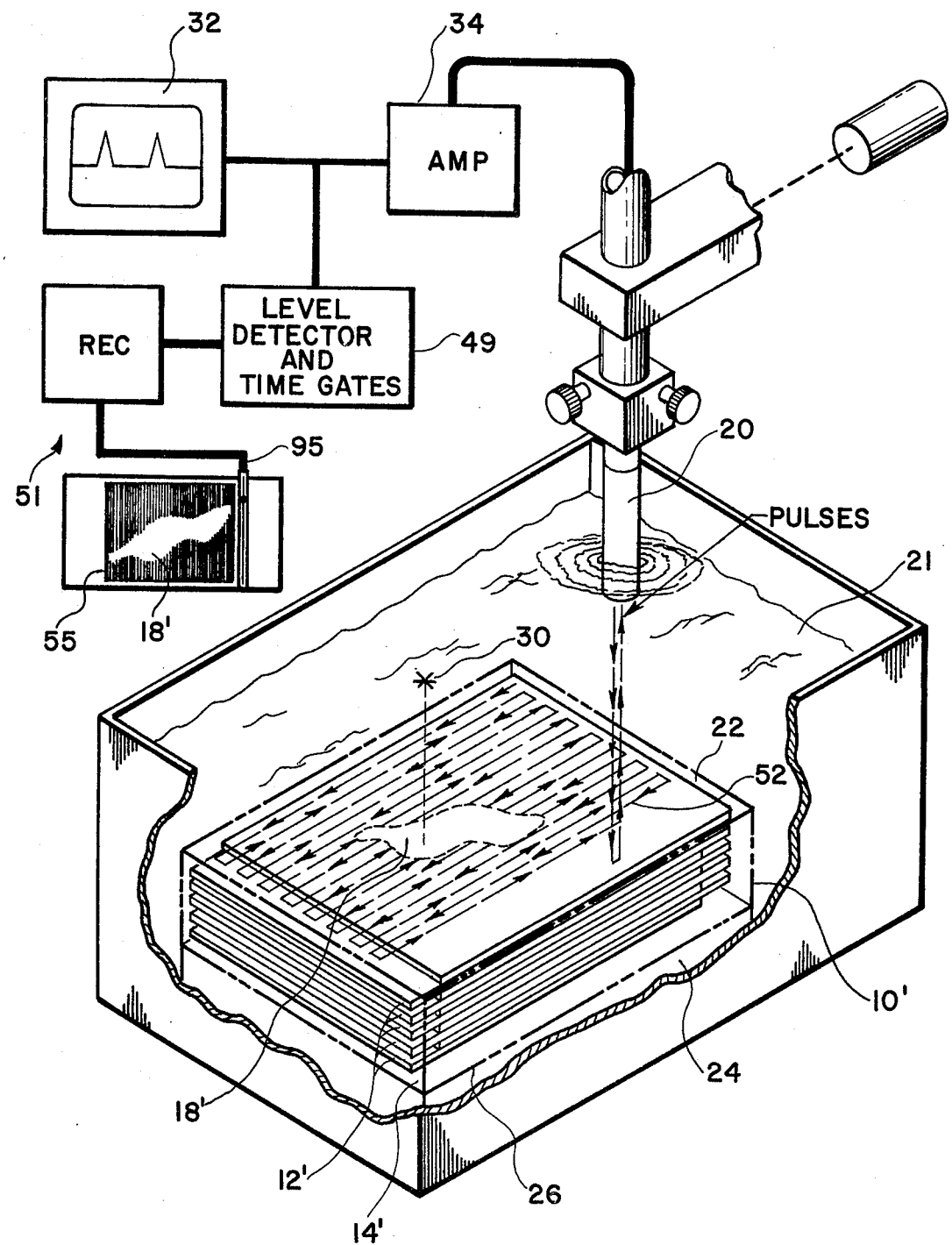
FIG. 2 illustrates schematically a technique for the detection of internal void defects in accordance with the present invention.

With reference to FIG. 2, a ceramic capacitor body to be tested for the presence of internal voids is indicated at 10' having parallel metal planar metal electrodes 12' separated by ceramic dielectric 14' and having a delamination defect indicated at 18' appearing in FIG. 2 between the second uppermost electrode and the underlying ceramic. A conventional transducer 20 capable of transmitting and receiving pulses of ultrasonic energy is arranged to transmit pulses of ultrasonic energy in a direction substantially perpendicular to face 22 of capacitor body 10' which is parallel to the metal electrodes 12'. Capacitor body 10' and transducer 20 are suitably immersed in water 21 to provide a coupling medium, in which the velocity of the ultrasonic pulse is substantially different from the velocity of the ultrasonic pulse in the capacitor body. Capacitor body 10' can be supported in contact with a substrate 24, for example, made of metals, e.g., aluminum or plastics such as polymethylmethacrylate, in which the transmission velocity of ultrasonic energy is substantially different from the velocity through capacitor body 10'. Alternatively, capacitor body 10' can be suspended in the water or other liquid or in contact at faces 22 and 26 with any medium having an ultrasonic transmission velocity substantially different from the transmission through the capacitor body, i.e., a difference of 15% or more which can be determined by routine measurements. Under such circumstances pulses of ultrasonic energy transmitted by transducer 20 through capacitor body 10' will be reflected at perpendicular bottom face 26 of capacitor body 10' and can be detected by transducer 20. In the event that there is no delamination in the path of the ultrasonic energy, for example, with transducer 20 located in the position shown in FIG. 2, a significant portion of the transmitted pulse of ultrasonic energy will be reflected from perpendicular face 26 of capacitor body 10' which can be detected by transducer 20. However, if transducer 20 is positioned at a location over a delamination defect 18', e.g., over location 30, energy reflected from face 26 will be very substantially reduced in magnitude since the pulse of ultrasonic energy transmitted by transducer 20 will be partially reflected by delamination 18', and very likely refracted due to non-perpendicular and irregular boundaries common to delaminations, and hence less transmitted ultrasonic energy reaches face 26. Also, the reflection of ultrasonic energy from face 26 must pass back through delamination 18' and can be further attenuated for the reasons noted above. Consequently, the magnitude of the reflected pulse from face 26 is very substantially different from the magnitude of a reflected pulse from face 26 when no delamination is in the path of transmitted ultrasonic energy. This multiple attenuation in the case of a delamination defect enables a clear comparison of the magnitude of reflected pulses to indicate the presence of a delamination defect.

Figure 3:
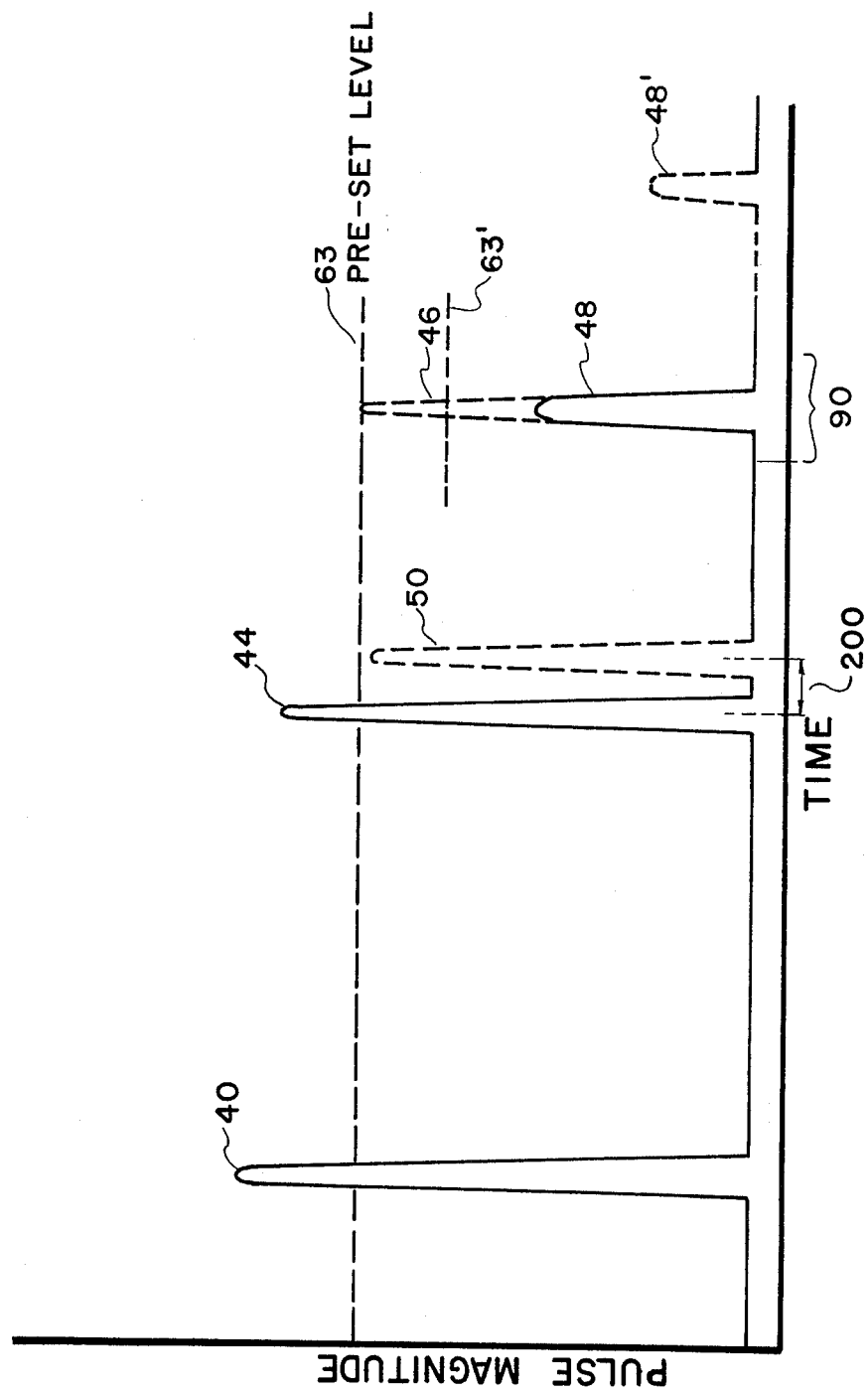
FIG. 3 illustrates ultrasonic transmissions and reflections utilized in the practice of the method of the present invention.
Figure 4A:
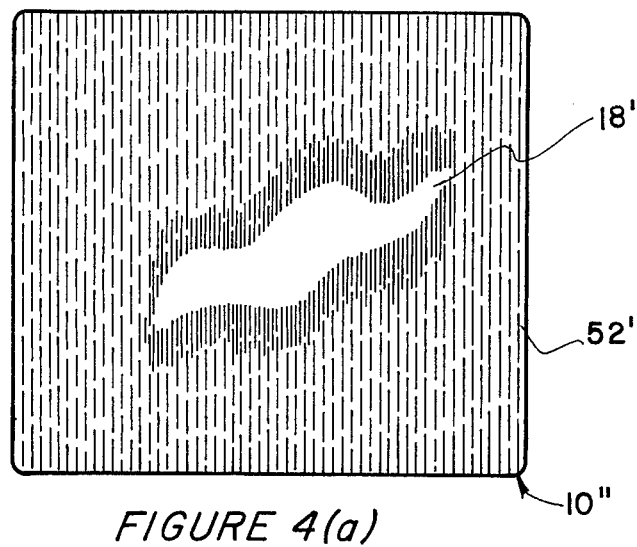
FIGS. 4 and 5 show visual displays obtainable in the testing method of the present invention.
Figure 4B:
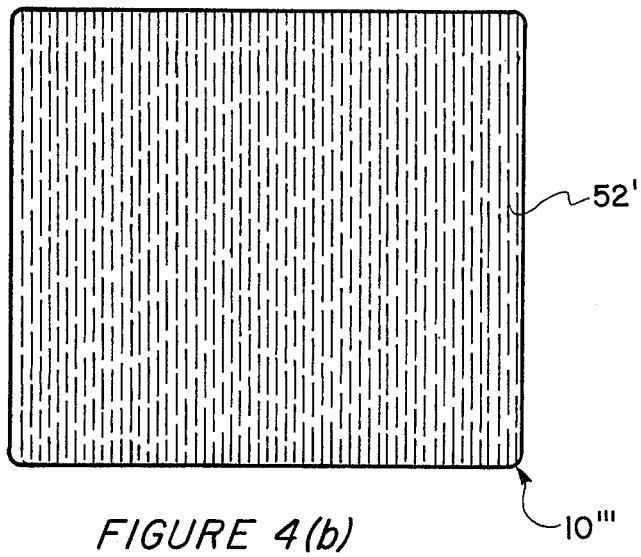

Further with reference to FIG. 2 in conjunction with FIG. 3, an ultrasonic pulse of energy transmitted by transducer 20 is indicated at 40 in FIG. 3, representing, for example, a visual display, for example, provided by oscilloscope 32. Oscilloscope 32 is conventionally electrically connected to transducer 20, suitably through an amplifier 34, and receives an electrical signal pulse corresponding to the transmitted pulse of ultrasonic energy, noted previously as 40 in connection with FIG. 3. With reference to FIG. 3, pulse 44 corresponds to the pulse of ultrasonic energy reflected from top face 22 of capacitor body 10' and received by transducer 20 and converted to an electrical signal for visual display at oscilloscope 32. Similarly, pulse 46 in FIG. 3 corresponds to the pulse of ultrasonic energy reflected from face 26 of capacitor body 10' when there is no delamination defect in the path of the transmitted pulse of ultrasonic energy. When the transducer 20 is located such that a delamination defect 18' is in the path of the transmitted pulse, the pulse 48 reflected from face 26 is, due to the multiple attenuation effect previously described, substantially less in magnitude from reflected pulse 46 and a comparison therebetween clearly shows the presence of a delamination defect. Pulse 50 represents the reflection pulse at the delamination defect 18' and can be readily distinguished from the reflection pulse 48 by routinely correlating the time base of FIG. 3 with the known thickness of capacitor body 10'. In practice, with reference to FIG. 2, a conventional pulse level detector arrangement 49 can be connected in circuit with recorder 51 so that only pulses above a set level, indicating no lamination defects, will actuate recorder 51 comprising a chart 55 and pen attachment 95. With transducer 20 mechanized to substantially completely traverse capacitor body 10', along the path indicated at 52 in FIG. 2, recorder 51 can provide a visual facsimile display of the lamination defect 18', for example, as illustrated in FIG. 4(a) and at 55 in FIG. 2 which is a chart responsive to pen attachment 95 of recorder 51, the pen attachment 95 being deactuated by recorder 51 when the pulse reflected from bottom face 26 is less than the pre-set level 63. FIG. 4(b) represents a capacitor body free of lamination defects as compared to FIG. 4(a) illustrating a lamination defect 18'. Commercial devices capable of being operated in the previously described manner are commercially available, e.g., LAB-SCANNER, manufactured by Automation Industries, Incorporated. Such devices are also capable of being gated so that only reflection pulses for time 90 in FIG. 3 are recorded so as to eliminate signals corresponding to other reflection pulses such as 50 and 48'; pulse 48' represents a reflection of pulse 48 back from upper face 22 after reflection from bottom face 26 and can be utilized for void detection if increased pulse discrimination is desirable.

Figure 5:
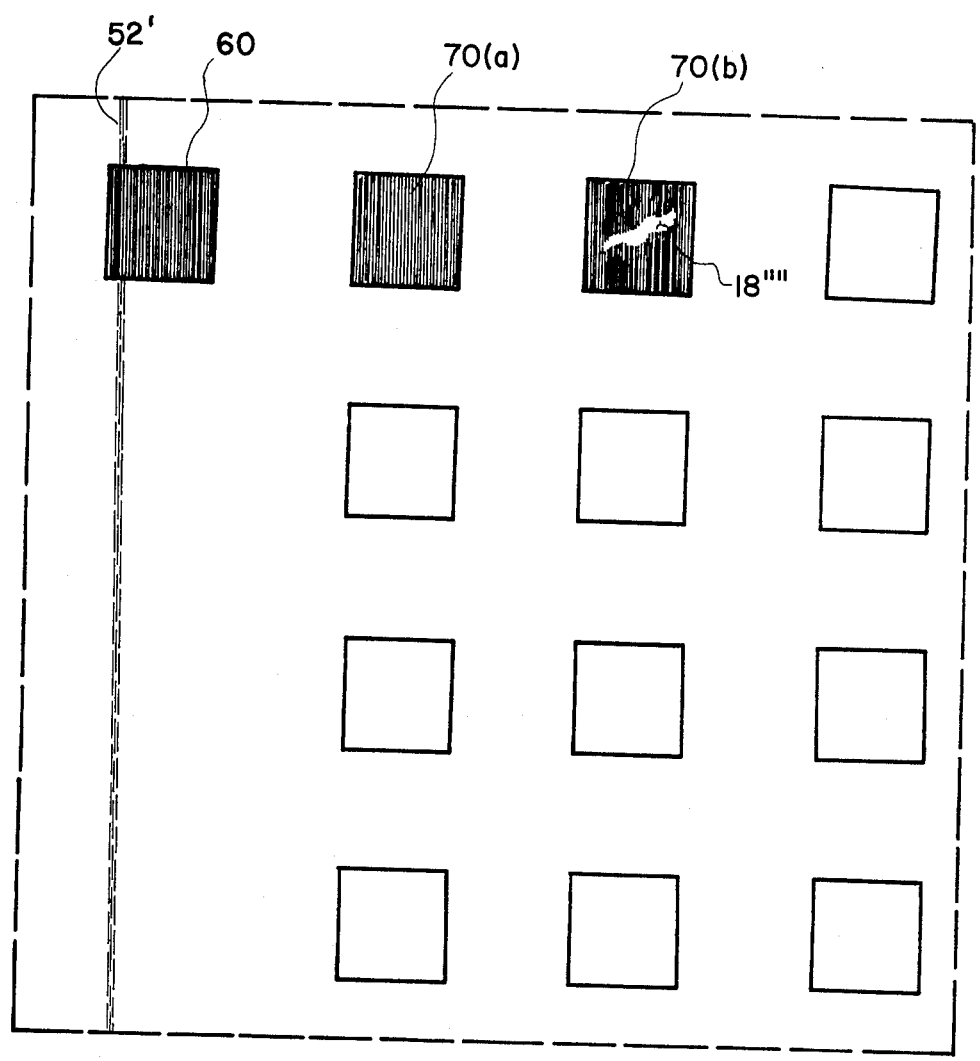

In a particular embodiment of the present invention, instead of a single capacitor body, an array of ceramic capacitor bodies to be tested can be arranged in a pattern similar to that of FIG. 5 (e.g., on a suitable substrate such as a metal block, e.g., aluminum, steel, or plastic sheet, e.g., polymethymethacrylate.) The array is positioned in a coupling medium in the same manner as a single capacitor body as illustrated in FIG. 1. Transducer 20 is mechanized to traverse the entire array of capacitor bodies as indicated at 52'. Since the commercial production of ceramic capacitors of a given design ordinarily involves many thousands of capacitors, it is convenient to select a particular ceramic capacitor body that is known to have long term reliability and to be free from defects associated with delaminations. Such a capacitor body can be used as a standard, indicated, for example, at 60 FIG. 5. Capacitor body 60 is subjected to ultrasonic pulse traversing as previously described, and Level Detector 49, indicated in FIG. 2, is set to provide a pre-set level of reflection pulse detection as indicated at 63 in FIG. 3; in this case, with reference to FIG. 3, pulse 46 indicates the reflection pulse of standard capacitor body 60. This arrangement provides a pulse magnitude with which the reflection pulses obtained by traversing capacitor bodies 70(a) and 70(b), etc., can be clearly compared as recorded at 70(a), 70(b), etc., in FIG. 5. If a reflection pulse is less than the set level 63, no mark will be made by pen 95 of recorder 51 on chart 55 and a white area will remain on chart 95 in the facsimile of the particular capacitor, e.g., 70(b), indicating a lamination defect 18'. FIG. 5 is representative of a visual display which can be provided by commercially available equipment such as that previously noted.

The present invention as previously described is based in part upon the discovery that ultrasonic energy, at convenient frequencies, e.g., 1 MHz to 5 MHz, can be used to obtain a standard, such standard being in the form of a reflection pulse along an inhomogeneous path through the entire body of a "sound" ceramic capacitor. Such a standard is obtainable since it has been found that the metal electrodes in a "sound" device do not themselves produce reflections of any significant magnitude as compared to the standard ultrasonic reflection pulse provided in accordance with the practice of the present invention. Further, the reflection pulse obtained when a void defect is present is multiply attenuated so as to provide a highly reliable indication of such defects. It has been determined that it is possible to clearly detect detrimental internal voids by the method hereinabove described regardless of the presence of dielectric-embedded electrodes, notwithstanding that each metal electrode to dielectric interface represents a potential site of ultrasonic energy scattering. Multilayer ceramic capacitor bodies of the type previously described have been successfully tested by the method of the present invention. The electrode metal of the tested ceramic capacitor bodies were materials containing at least about 20% Pd, up to about 40% Pt, balance Au. The dielectric materials of the capacitor body contained from about 18% to 93% barium titanate together with customary commercial dielectric property modifiers.

Figure 6:
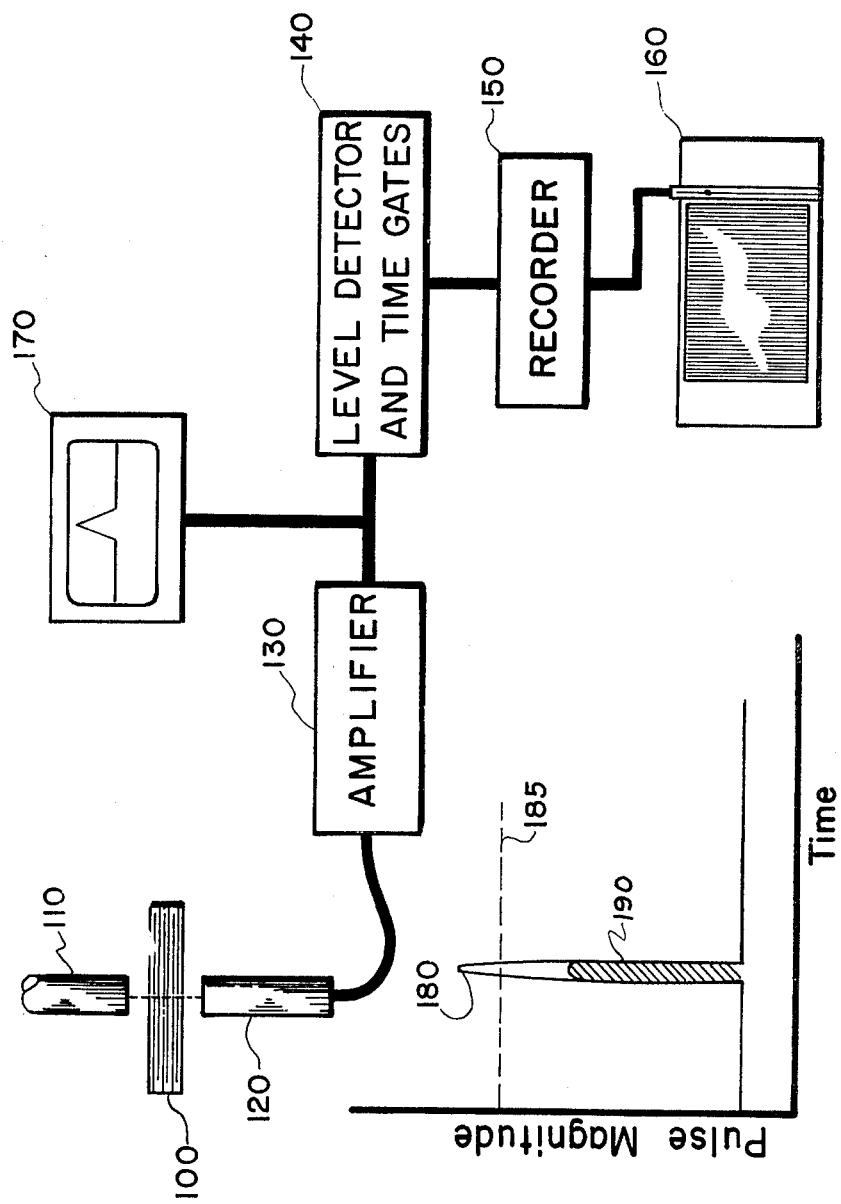
FIG. 6 shows a further embodiment of the present invention.

In a further embodiment of the present invention, the ultrasonic energy which is transmitted completely through a multilayer ceramic capacitor body is utilized to determine the presence or absence of detrimental internal voids. With reference to FIG. 6 (a), a multilayer ceramic capacitor body 100 is placed, as shown, in the path between a transmitting transducer 110, adapted to transmit ultrasonic energy, and a receiving transducer 120, adapted to receive ultrasonic energy and convert the received ultrasonic energy into a visual display by way of amplifier 130, level detector and time gate arrangement 140, recorder 150 and pen and chart arrangement 160, such equipment being suitably of the type described in conjunction with FIG. 2. With a standard multilayer ceramic capacitor body, void free, located in the position of capacitor body 100, a pulse of ultrasonic energy transmitted from transducer 110 passes through the capacitor body and is detected by receiving transducer 120 and converted to an electrical signal which is displayed at oscilloscope 170. FIG. 6(b) shows at 180 a representation of the magnitude of the pulse received by receiving transducer 120. Level detector arrangement 140 is adjusted to lower level, such as indicated at 185. When a capacitor body having a detrimental void defect is in position at 100, the ultrasonic energy received by receiving transducer 120 is represented at 190 in FIG. 6(b) Recorder 150 and chart arrangement 160 can then provide a visual display of the detrimental void in the manner previously described in conjunction with FIG. 2. This embodiment of the present invention requires an additional ultrasonic transducer and does not take advantage of the multiple attenuation effect of the embodiment of FIG. 2.

In a further embodiment of the present invention, referring to FIG. 3 and the apparatus of FIG. 2, the pulse indicated as 50 represents the reflection pulse of ultrasonic energy from the void 18', as previously mentioned and this pulse can be displayed on oscilloscope 32, together with pulse 44, which represents the reflection pulse from the top surface of the capacitor body 10' in FIG. 2. The time interval 200 thus corresponds to the depth location of void 18' in FIG. 2 and can be routinely correlated to the actual location of the defect in the multilayer ceramic capacitor body. In this embodiment, no advantage is taken of the multiple attenuation effect which is utilized when the previously employed "bottom surface" reflection embodiment is used for void detection. Also, the use of pulse 50 for void detection is essentially limited to planar type defects which reflect a detectable amount of ultrasonic energy.

The following example will further illustrate the present invention.

EXAMPLE

An array of 12 multilayer ceramic capacitors, each having dimensions of about 10mm × 12mm in the plane of the electrodes, and about 3mm thick were placed on a ⅝ inch thick sheet of polymethymethacrylate and placed submerged in water in an Automation Industries, Incorporated, LAB-SCANNER in the manner indicated in FIG. 2. Using the above equipment, pulses of ultrasonic energy provided by a 10 MHz transducer with a 40mm focal distance and a nominal 1mm resolution were used in conjunction with a 0.4mm spacing between traversing scan lines and the recorder arrangement was set to provide a "trace" when no void was detected as described hereinbelow. Each of the capacitor bodies tested had the following configuration:

| | |
|---|---|
| Electrodes | 24 |
| Electrode thickness | 3 microns-nominal |
| Electrode material | Palladium |
| Dielectric material | 86% barium titanate balance modifiers including calcium zirconate and tantalum pentoxide |
| Dielectric thickness | 100 microns - nominal |

Figure 7:
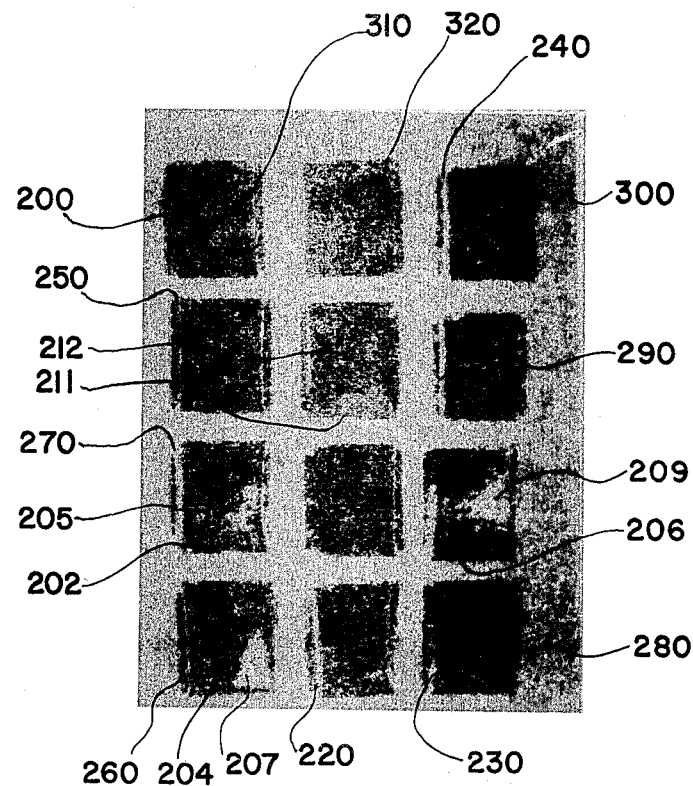
FIG. 7 shows a chart record visual display obtained in accordance with the method of the present invention.

The chart record obtained by traversing the array is shown in the photograph of FIG. 7. In FIG. 7, capacitor body 200, determined to be in a void-free condition by the method of the present invention was chosen as a standard and the level detector of the apparatus above-noted was set to interrupt the chart trace whenever the reflection pulse magnitude from the bottom surface of the capacitor body (exemplified by pulse 48 in FIG. 3) was 80% or less than the bottom reflection pulse magnitude for the standard capacitor body 200 (exemplified by pulse 46 in FIG. 3). That is to say, the "pre-set level" 63 of FIG. 3 was lowered, as indicated at 63', from the level 63 which increased the sensitivity of recorder for an initial test of the array. In the chart shown in FIG. 7, capacitor bodies 202, 204 and 206 represent capacitor bodies having detrimental internal voids indicated by the "white" areas 205, 207 and 209. The small "white" spot 211 appearing in the capacitor body chart record 212 does not suggest a detrimental void in view of its small size and regular configuration. In such a case, re-testing and examination of the suspect capacitor body is warranted. In the test of this example, the capacitor bodies tested were previously provided with metallized terminals such as indicated at 16 in FIG. 1. Due to the irregularity of the surface resulting from the applied metallization, the "white" lines indicated for example at 220, 230, 240, 250, 260, 270, 280, 290, 300, 310 and 320 appear in the chart record. These "white" lines do not represent detrimental voids and are typical of records obtained with metallized capacitor bodies due to scattering of ultrasonic energy from the irregular surface resulting from metallization.

Figure 8A:
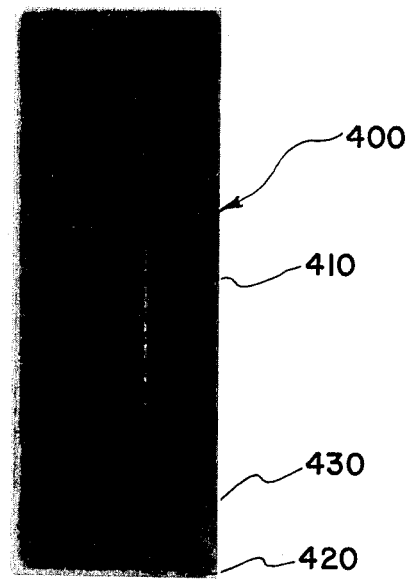
FIGS. 8(a) and 8(b) are photographs of cross sections of multilayer ceramic capacitor bodies.
Figure 8B:
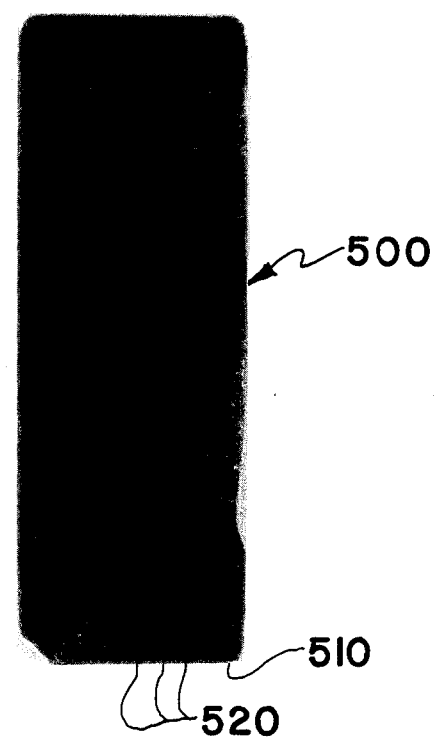

With reference to FIGS. 8(a) and 8(b), FIG. 8(a) shows a photograph of a multilayer capacitor body 400 which was determined to have a detrimental void by the practice of the present invention following a procedure similar to the foregoing example. The capacitor body was sectioned and revealed a delamination type void indicated at 410. In FIG. 8(a), the electrodes of the capacitor are indicated at 420 and the dielectric at 430. FIG. 8(b) shows a photograph of a sectioned capacitor body 500 which was determined to be void free by the method of the present invention following a procedure similar to that of the above example. No detrimental voids are observable in the capacitor body of FIG. 8(b) wherein the ceramic dielectric is indicated at 510 and the electrodes by the dark strips 520.

What is claimed is:

1. A method of determining the presence of detrimental void defects in a multilayer ceramic capacitor body having a pair of parallel opposed surfaces and having a plurality of planar metal electrodes, the planar surfaces of said metal electrodes being arranged parallel to said parallel opposed surfaces and separated by and completely enclosed within ceramic dielectric said method comprising transmitting ultrasonic energy at a selected ultrasonic frequency into a fired ceramic capacitor body having from about 5 to 100 planar parallel metal electrodes, said electrodes being from about 2 to 10 microns thick and separated from each other by about 15 to 100 microns of ceramic, the direction of said ultrasonic energy being substantially perpendicular to a surface of said capacitor body and to said planar metal electrodes; detecting a portion of said ultrasonic energy which passes through said metal electrodes and said ceramic dielectric and emerges from said capacitor body; and comparing the magnitude of said portion of ultrasonic with a predetermined magnitude to provide an indication of the presence in said capacitor body of a detrimental void defect having a dimension parallel to said electrodes as small as 100 microns and a thickness as small as 5 microns.

2. Method for determining the presence of detrimental void defects in a multilayer ceramic capacitor body having a pair of parallel opposed surfaces and having a plurality of planar metal electrodes, the planar surfaces of said metal electrodes being arranged parallel to said parallel opposed surfaces and separated by and completely enclosed within ceramic dielectric said method comprising transmitting a pulse of ultrasonic energy at a selected ultrasonic frequency into a fired ceramic capacitor body having from about 5 to 100 planar parallel metal electrodes, said electrodes being from about 2 to 10 microns thick and separated from each other by about 15 to 100 microns of ceramic, the direction of said transmitted ultrasonic energy being substantially perpendicular both to one of said pair of parallel opposed surfaces of the multilayer ceramic capacitor body and to said planar metal electrodes to provide a reflection pulse of ultrasonic energy from the location where said transmitted pulse of ultrasonic energy leaves said multilayer ceramic capacitor body at said other parallel opposed surface of said ceramic capacitor body, said reflection pulse being reflected back along substantially the same direction as the transmitted pulse, detecting said reflection pulse after said reflection pulse exits said ceramic capacitor body at the surface where said transmitted pulse entered said capacitor body, and comparing the magnitude of said reflection pulse with a predetermined magnitude corresponding to a reflection pulse for a void-free capacitor body, reflection pulse magnitude less than said predetermined to provide an indication of the presence in said capacitor body of a detrimental void defect having a dimension parallel to said electrodes as small as 100 microns and a thickness as small as 5 microns.

3. Method in accordance with claim 2 wherein a sequence of ultrasonic pulses are transmitted through said face of said capacitor body, said pulses being directed so as to substantially completely traverse said capacitor body at intervals less than a predetermined maximum tolerable void dimension to provide a traverse of reflection pulses.

4. Method in accordance with claim 3 wherein the reflection pulses obtained for each of said transmitted pulses are converted into corresponding electrical signals, each of said signals corresponding to ultrasonic reflection pulses having a magnitude less than said predetermined magnitude being adapted to provide an electrical indication of the presence of a void defect in said capacitor body.

5. A method in accordance with claim 4 wherein said electrical signals are converted into a visual display corresponding to said traverse of reflection pulses wherein the display of electrical signals corresponding to reflection pulse having a magnitude less than said predetermined magnitude are visually distinguishable from the display of the other pulses.

6. A method in accordance with claim 5 wherein said visual display is in the form of a permanent chart record.

* * * * *